United States Patent [19]

Campbell et al.

[11] Patent Number: 5,302,707
[45] Date of Patent: Apr. 12, 1994

[54] 5-FLUOROURIDINE NUCLEOSIDE PHOSPHATE COMPOUNDS

[75] Inventors: David A. Campbell; Mark A. Gallop, both of East Palo Alto, Calif.

[73] Assignee: Affymax Technologies N.V., Palo Alto, Calif.

[21] Appl. No.: 858,298

[22] Filed: Mar. 26, 1992

[51] Int. Cl.$^5$ .............................................. C07H 19/06
[52] U.S. Cl. .............................. 536/25.33; 536/25.34; 536/26.8; 536/28.53; 536/28.55; 435/6; 435/69.1; 435/69.3; 435/70.2; 435/89; 435/188.5; 435/240.27; 530/388.9
[58] Field of Search ................... 536/26.7, 26.8, 25.3, 536/25.34, 25.33, 28.53, 28.55; 514/50, 51, 885; 435/6, 69.3, 70.2, 70.21, 89, 188.5, 240.27; 530/338, 337

[56] References Cited

U.S. PATENT DOCUMENTS

| | | |
|---|---|---|
| 4,671,958 | 6/1987 | Rodwell et al. ................. 424/85 |
| 4,888,281 | 12/1989 | Schochetman et al. .......... 435/72 |
| 4,900,674 | 2/1990 | Benkovic et al. ............... 435/188.5 |

FOREIGN PATENT DOCUMENTS

| | | |
|---|---|---|
| 0187658 | 7/1986 | European Pat. Off. . |
| 0251093 | 1/1988 | European Pat. Off. . |
| WO89/10754 | 11/1989 | PCT Int'l Appl. . |
| WO91/14769 | 10/1991 | PCT Int'l Appl. . |

OTHER PUBLICATIONS

Killion et al. (1989) Sem. Oncol., 16:106-115.
Bagshawe et al. (1988) Br. J. Cancer, 58:100.
Bagshawe (1987) Br. J. Cancer, 56:531.
Pollack et al. (1986) Science, 234:1570-73.
Pollack et al. (1987) Cold Spring Harbor Symp. Quant. Biol., 52:97-104.
Pollack et al. (1989) J. Am. Chem. Soc., 111:1929-1931.
Jacobs et al. (1987) J. Am. Chem. Soc., 109:2174-2176.
Tramontano et al. (1986) Science, 234:1566-1570.
Tramontano et al. (1988) J. Am. Chem. Soc., 110:2282-2286.
Janda et al. (1988) Science, 241:1188-1191.
Napper et al. (1987) Science, 237:1041-43.
Jackson et al. (1988) J. Am. Chem. Soc., 110:4841-42.
Janda et al. (1988) J. Am. Chem. Soc., 110:4835-37.
Hilvert et al. (1988) Proc. Natl. Acad. Sci. USA, 85:4953-55.
Benkovic et al. (1988) Proc. Natl. Acad. Sci. USA, 85:5355-58.

*Primary Examiner*—Johnnie R. Brown
*Assistant Examiner*—J. Oliver Wilson
*Attorney, Agent, or Firm*—James M. Heslin; Kevin R. Kaster; Lauren L. Stevens

[57] ABSTRACT

Compositions and methods for producing the activating moiety of a site-directed catalytic antibody are provided The activating moiety serves to enhance the rate of chemical reactions involving the conversion of the prodrug to one or more active substrates or drugs. The activating moiety typically comprises a catalytic antibody. Compositions and methods for producing the catalytic antibodies, as well as the haptens which are used to generate the catalytic antibodies, are provided. Compositions and methods for producing the prodrugs are also provided.

8 Claims, No Drawings

5-FLUOROURIDINE NUCLEOSIDE PHOSPHATE COMPOUNDS

BACKGROUND OF THE INVENTION

1. Field of the Invention

This invention relates generally to methods for the site-directed activation of prodrugs. More particularly, the invention relates to the administration of a prodrug in conjunction with a site-directed catalytic antibody which converts the prodrug to an active drug.

2. Description of the Background Art

Many efforts have been made to increase the selectivity of drugs by creating prodrug versions whereby the activity of the drug is attenuated by some pendent group. For a review of these efforts, see Bundgaard, H., ed., (1985) *Design of Prodrugs*, Elsevier Science Publishers, Amsterdam. The prodrug is envisioned to undergo either spontaneous degradation or, preferably, enzymatic conversion to the active form. Theoretically, selectivity can be increased by relying on an enzyme that is over-produced by, or is only present at, the target cells. However, despite the appeal of this approach, this strategy has not proven widely successful, primarily due to the difficulty of identifying enzymes specific to the target cells.

Attempts have also been directed to site specific drug delivery utilizing monoclonal antibodies. These drug delivery systems employ a cytotoxic agent which has been conjugated directly to an antibody recognizing the desired antigen. Utilizing this method, radioisotopes, drugs, and biotoxins have been conjugated to monoclonal antibodies, and selective cytotoxicity has been observed. This method is described generally by Borrebaeck et al. (Eds.) (1990) *Therapeutic Monoclonal Antibodies*, Stockton Press: New York.

The use of antibody-targeted site specific drug delivery suffers from many drawbacks. The most obvious shortcoming results from the heterogeneity in distribution of the antigen amongst targeted cells. Not all target cells may produce the antigen, thus, allowing some target cells to escape. Moreover, cells in poorly vascularized sites, such as in a tumor mass, are virtually inaccessible to the antibody. Thus, these cells will also escape treatment. Further, the slow clearance of antibodies from the body, with half-lives typically on the order of a few days, contributes to cytotoxic effects in normal cells.

In addition, the use of antibody-targeted drugs relies on endocytosis of the conjugate, followed by degradation in the lysosomes to release the drug inside the targeted cells. The rates of internalization of the conjugates by various cancer cells have been studied (Killion, et al. (1989) *Seminars in Oncology*, 16:106-115) and shown to be highly variable, with some cells exhibiting minimal uptake of the conjugates. Finally, the acidic pH of the lysosomes limits this technique to acid stable drugs.

A further approach to site specific drug delivery utilizes antibody directed enzymes. Antibodies which are capable of recognizing the target cells are coupled to enzymes which are capable of unmasking a prodrug. After localization of the enzyme/antibody conjugate at the target cells, the prodrug is administered and rendered cytotoxic at the target site. This approach has been described by Bagshawe et al. (1988) *Br. J. Cancer*, 58:100; and Bagshawe (1987) *Br. J. Cancer*, 56:531.

The antibody directed enzyme approach has been expanded upon by Haber et al. European Patent Pub. No. 0,187,658. Haber describes the site-specific activation of an inactive toxic agent by an antibody bound to an activator. The activator activates the inactive toxic agent by reacting chemically, allosterically or enzymatically with the inactive substance.

Powell et al. PCT patent publication No. WO89/10754 has suggested that catalytic antibodies may be "site specific" in that they are deliberately designed only to catalyze cleavage of bonds having certain structural conformations at specific sites in a biomolecule. Powell does not describe a protocol for targeted drug release at specific target sites The preparation of catalytic antibodies against haptens that are transition state analogs is described in the following references: Pollack et al. (1986) *Science*, 234:1570-1573; Pollack and Schultz (1987) *Cold Spring Harbor Symp. Quant. Biol.*, 52:97-104; Pollack and Schultz (1989) *J. Am. Chem. Soc.*, 111:1929-1931; Jacobs et al. (1987) *J. Am. Chem. Soc.*, 109:2174-2176; Tramontano et al. (1986) *Science*, 234:1566-1570; Tramontano et al. (1988) *J. Am. Chem. Soc.*, 110:2282-2286; Janda et al. (1988) *Science*, 241:1188-1191; Schochetman et al. (1989) U.S. Pat. No. 4,888,281; Benkovic et al. (1990) U.S. Pat. No. 4,900,674; Napper et al. (1987) *Science* 237:1041-43; European Patent Pub. No. 0,251,093; and Paul et al. PCT patent publication No. 91/14769.

The use of catalytic antibodies to overcome entropic barriers involved in orienting reaction partners is described in the following references: Jackson et al. (1988) *J. Am. Chem. Soc.*, 110:4841-4842; Janda et al. (1988) *J. Am. Chem. Soc.*, 110:4835-4837; Hilvert et al. (1988) *Proc. Natl. Acad. Sci. USA*, 85:4953-4955; and Benkovic et al. (1988) *Proc. Natl. Acad. Sci. USA*, 85:5355-5358.

The disclosures of the above cited references and other references referred to throughout this application are incorporated herein by reference.

SUMMARY OF THE INVENTION

The present invention provides compositions and methods for producing the activating moiety of a site-directed catalytic antibody. The activating moiety serves to enhance the rate of chemical reactions involving the conversion of the prodrug to one or more active substrates or drugs In the exemplary embodiment, the activating moiety will enhance the hydrolysis of specific ester bonds in the prodrug to produce the active drug.

The activating moiety usually comprises a catalytic antibody. Catalytic antibodies may be prepared by producing antibodies to an immunogen, wherein the immunogen comprises a hapten bound to a carrier molecule. The hapten will preferably comprise a reactant or reactive intermediate analog, typically a transition state analog, involved in the chemical reaction of interest.

The present invention is directed towards the hapten and immunogens which may be used to prepare the activating moiety. Accordingly, one embodiment of this invention comprises a compound having the formula

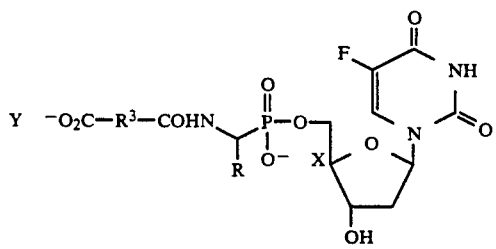

in which R is hydrogen, alkyl, aryl, heteroaryl, or arylalkyl; $R^3$ is alkyl; and X and Y are independently hydrogen, an alkali metal counterion, or a counterion derived from an organic base. In a preferred embodiment, R is isopropyl, $R^3$ is $-(CH_2)_2-$, and X and Y are lithium.

A further embodiment of this invention is a compound having the formula

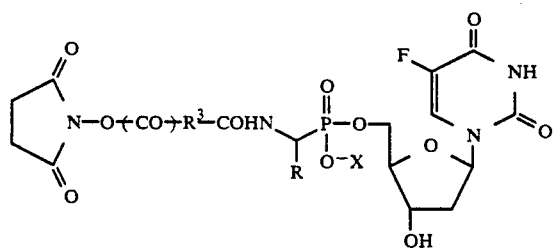

in which R is hydrogen, alkyl, aryl, heteroaryl, or arylalkyl; $R^3$ is alkyl; and X is hydrogen, an alkali metal counterion, or a counterion derived from an organic base. In a preferred embodiment, R is isopropyl, $R^3$ is $-(CH_2)_2-$, and X is lithium.

The invention is also directed to the catalytic antibodies which may be elicited from the above haptens and immunogens. Conveniently, monoclonal antibody techniques will be utilized in order to obtain a source of homogeneous catalytic antibodies of uniform specificity. Alternatively, antibody fragments and/or polypeptides which mimic the binding specificity of the catalytic antibody can be prepared and utilized.

A further aspect of this invention comprises compositions and methods for preparing the prodrugs. The exemplary embodiment provides for a prodrug having a formula

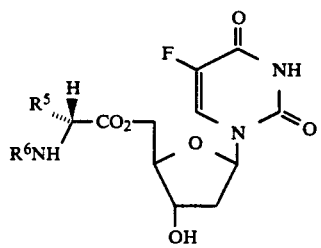

in which $R^5$ is hydrogen, alkyl, aryl, heteroaryl, or arylalkyl and $R^6$ is hydrogen or a terminal amino protecting group.

DESCRIPTION OF THE SPECIFIC EMBODIMENTS

1. Definitions and General Parameters

Unless otherwise stated, the following terms used in the specification and claims have the meanings given below:

In its broadest sense, the term "antigen" is defined as a molecule which induces the formation of an antibody. As used herein, "antigen" means a molecule which is inherently immunogenic, a hapten according to the invention or an immunogen which comprises a hapten according to the invention coupled to a carrier molecule by a suitable coupling moiety. Carrier molecules include, for example, keyhole limpet hemocyanin (KLH), thyroglobulin, chicken immunoglobulin, ovalbumin, bovine serum albumin (BSA), T-helper peptides, etc. "Coupling moieties" refers to biotechnological cross-linking reagents well known in the art (e.g., commercially available from Pierce, Rockford, Ill.), and include, for example, disuccinyl suberate.

"Antibody" includes whole immunoglobulins and fragments thereof which contain the binding site for the antigen.

A "catalytic antibody" is an antibody or fragment thereof which is capable of enhancing the rate of a chemical reaction. The catalytic antibody does not enter into the chemical reaction, and thus, is not consumed in the reaction.

"Hapten" refers to a molecule which acts as an antigen. In general, haptens are obtained in the form of racemates or mixtures of diastereomers. If desired, techniques well known in the art for the separation of the mixtures into stereochemically homogeneous constituents may be used. Preparation of the optical isomers in a pure state is also possible by using stereochemically homogeneous starting materials.

"Prodrug" refers to a compound that is converted into a therapeutically active drug by metabolic or other chemical processes within the body. A prodrug is typically substantially less active than the active drug to which the prodrug corresponds.

"Active drug" refers to any of a variety of substances which might be deemed useful in the treatment of target sites. A particularly preferred active drug is 5-fluorouridine.

"Alkali metal" refers to a metal in Group 1A of the Periodic Table, i.e., lithium, sodium, and potassium. "Alkali metal salt" refers to a salt of carboxylic or phosphonic acids formed with alkali metals or alkali metal bases, such as alkali metal hydroxides and alkali metal alkoxides "Alkali metal counterion" refers to the positively charged ion of the alkali metal salt.

"Organic base salt" refers to a salt of a carboxylic or phosphonic acid formed with organic bases such as trimethylamine, diethylamine, ethanolamine, piperidine, isopropylamine, choline, caffeine, and the like. "Counterion derived from an organic base" refers to the positively charged ion of the organic base salt.

"Protecting group" refers to a chemical group which exhibits the following characteristics: 1) the group must react selectively with the desired functionality in good yield to give a protected substrate that is stable to the projected reactions; 2) the protecting group must be selectively removable from the protected substrate to yield the desired functionality; and 3) the protecting group must be removable in good yield by reagents that do not attack the other functional group(s) generated in such projected reactions. Examples of protecting groups can be found in Greene et al. (1991) *Protective Groups in Organic Synthesis,* 2nd Ed., John Wiley & Sons, Inc., New York. Preferred terminal amino protecting groups include N-benzyloxycarbonyl and acetyl. A particularly preferred hydroxyl protecting group for primary hydroxyls is dimethyoxytrityl. A particularly preferred hydroxyl protecting group for secondary hydroxyls is t-butyldimethylsilyl.

"Alkyl" refers to a cyclic, branched, or straightchain aliphatic group containing only carbon and hydrogen. This term is further exemplified by groups such as methyl, heptyl, —(CH$_2$)$_2$—, and adamantyl. Alkyl groups can either be unsubstituted or substituted with one or more non-interfering substituents, e.g., halogen, alkoxy, acyloxy, hydroxy, mercapto, carboxy, benzyloxy, phenyl, or benzyl, each optionally substituted with additional non-interfering substituents. The term "non-interfering" characterizes the substituents as not adversely affecting any reactions to be performed in accordance with the process of this invention.

"Lower alkyl" refers to an alkyl group of one to six carbon atoms. Lower alkyl groups include those exemplified by methyl, ethyl, n-propyl, i-propyl, n-butyl, t-butyl, i-butyl (2-methylpropyl), cyclopropylmethyl, i-amyl, n-amyl and hexyl. Preferred lower alkyls are methyl and ethyl. If more than one alkyl group is present in a given molecule, each may be independently selected from "lower alkyl" unless otherwise stated.

"Aryl" refers to a monovalent unsaturated aromatic carbocyclic group having a single ring (e.g., phenyl) or multiple condensed rings (e.g., naphthyl or anthryl), which can optionally be unsubstituted or substituted with hydroxy, lower alkyl, alkoxy, chloro, halo, mercapto, and other non-interfering substituents.

"Heteroaryl" or "HetAr" refers to a monovalent unsaturated aromatic carbocyclic group having a singly ring (e.g., pyridyl or furyl) or multiple condensed rings (e.g., indolizinyl or benzo[b]thienyl) and having at least one hetero atom, such as N, O or S, within the ring, which can optionally be unsubstituted or substituted with hydroxy, alkyl, alkoxy, halo, mercapto, and other non-interfering substituents.

"Arylalkyl" refers to the groups —R"—Ar and —R'—HetAr, where Ar is an aryl group, HetAr is a heteroaryl group, and R" is straight-chain or branched-chain aliphatic group. Examples of arylalkyl groups include the sidechains of the amino acids phenylalanine and tryptophan.

"Carboxyalkyl" refers to the group —C(O)—R", where R" is lower alkyl

"Acyloxy" refers to the group —OC(O)R", where R" is alkyl.

"Effective amount" refers to an amount sufficient to induce a desired biological result. That result may be alleviation of the signs, symptoms, or causes of a disease, or any other desired alteration of a biological system.

Isolation and purification of the compounds and intermediates described herein can be effected, if desired, by any suitable separation or purification procedure such as, for example, filtration, extraction, crystallization, column chromatography, thin-layer chromatography, thick-layer (preparative) chromatography, distillation, or a combination of these procedures. Specific illustrations of suitable separation and isolation procedures can be had by reference to the examples hereinbelow. However, other equivalent separation or isolation procedures can, of course, also be used.

Compounds of formula 10 are named and numbered as illustrated. For example, a compound of formula 10 where R is isopropyl and R$^3$ is —(CH$_2$)$_2$— is named 2'-deoxy-5'-O-[[1-[N-[3-(N-hydroxysuccinimidylcarboxy)propionyl]-2-methylpropyl]phosphoryl]-5-fluorouridine.

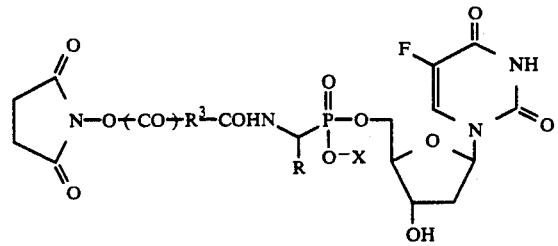

Site-Directed Catalytic Antibodies

According to the present invention, site-directed catalytic antibodies include a targeting moiety and an activating moiety joined together by a linker region. The targeting moiety is capable of specifically binding to a disease target site while the activating moiety is capable of enhancing the rate of a chemical reaction, specifically, the conversion of a prodrug into an active drug. The linker region is selected to maintain the activating moiety in a conformation capable of activating the prodrug when the targeting moiety is bound to the target site.

The Target Site

The target site may be any site for which it is deemed that initiation of therapy is appropriate. Such sites may be those arising from a pathogenic state induced by, for instance, a virus or a bacterium; a tumor; or the result of a dysfunction of a normal host system as, for example, the formation of a thrombus. The target site must, however, be a target for the targeting moiety of the site-directed catalytic antibody. For example, the target site may be a protein or glycoprotein capable of being bound by the site-directed catalytic antibody.

The Targeting Moiety

The targeting moiety provides for localization of the activating moiety at the target site. The targeting moiety will usually be a polypeptide, although it will also be possible to use small molecules designed to bind the target site, as discussed below. Preferred polypeptides include intact immunoglobulins or their fragments, such as Fv, Fab, F(ab)$_2$, or single chain Fv's. Most preferably, the immunoglobulins are monoclonal antibodies of the IgM or IgG isotype, of mouse, human or other mammalian origin.

The targeting moiety can also be a peptide or protein ligand for a cell surface receptor (e.g., interleukin-2). Other proteins or agents capable of binding to target sites, including growth factors, hormones and other ligands for naturally occurring receptors, may be used.

In addition to the polypeptide targeting moieties just described, the present invention may employ other small synthetic compounds that have an adequate binding affinity and specificity to the target sites of interest. The identification of these small synthetic compounds can be achieved through the use of techniques known to those working in the area of drug design.

Preparation of these identified molecules will depend on their structure and other characteristics and may normally be achieved by standard chemical synthesis techniques.

The Activating Moiety

The activating moiety will be selected to enhance the rate of a chemical reaction, specifically, the conversion of a prodrug into an active drug. The activating moieties of the present invention will usually be able to promote a chemical reaction by binding to a transition state involved in the chemical reaction, stabilizing the transition state and thereby enhancing the reaction rate.

Preferably, the activating moiety will consist of a catalytic antibody which possesses a binding site with affinity for at least one reactant, reactive intermediate, or transition state analog of the chemical reaction of interest. Intact catalytic antibodies or antibody fragments, such as Fv, Fab, F(ab)$_2$, or single chain Fv's, may be used as the activating moiety Catalytic antibodies having the desired binding site configuration based on the geometry and electronic configuration of the reactant, reactive intermediate, or transition state are most easily prepared by raising antibodies against a reactant, reactive intermediate, or transition state analog which is involved in the chemical reaction of interest. Conveniently, the reactant, reactive intermediate, or transition state analog is prepared and utilized as a hapten in preparing the antibodies having desired affinities and catalytic activities.

Catalytic antibodies may be elicited through both in vivo and in vitro techniques. The skilled artisan will readily appreciate that when in vitro elicitation is involved, the haptens of the present invention, by themselves, may be used to elicit the catalytic antibodies. When elicitation is achieved through in vivo techniques, it is understood that immunogens comprising haptens complexed to a suitable carrier molecule are used to elicit the catalytic antibodies.

Broadly, the techniques involve exposing cells capable of producing antibodies to the antigen and thereby generating antibody producing cells; immortalizing the antibody producing cells typically by fusion with myeloma cells and thereby producing a plurality of hybridoma cells, each producing monoclonal antibodies; and screening the monoclonal antibodies to identify a monoclonal antibody which catalyzes the chemical reaction of interest. The monoclonal antibody so identified may then be replicated, again by either in vivo or in vitro techniques, to obtain a quantity sufficient to catalyze the chemical reaction of interest.

Catalytic monoclonal antibodies are elicited in vivo by modification of the technique disclosed by Koprowski et al, (1980) U.S. Pat. No. 4,196,265, which is hereby incorporated by reference. The details of that process are known in the art. A series of monoclonal antibodies directed to a specific molecule is prepared under suitable conditions This involves first immunizing the host, such as BALB/C mice, with an appropriate antigen. The antigen comprises a hapten according to the invention bound to a peptide or other carrier molecule.

Antibody-producing lymphocytes are then removed from the spleens of the immunized host and hybridized with myeloma cells, such as SP2/0 cells, to produce hybridoma cells. These hybridoma cells are then placed in the wells of microtiter plates. The series of monoclonal antibodies being produced by the hybridoma cells is screened under appropriate conditions to identify monoclonal antibodies which catalyze the desired reaction under appropriate conditions.

Screening may be conveniently accomplished by treating a standardized solution of the reactant (i.e., the prodrug) with an aliquot of medium withdrawn from a microtiter well and measuring the presence of the desired product (i.e., the drug or active substrate) by conventional instrumental methods. This measurement may be readily conducted, for example by spectrophotometric methods or by gas-liquid or high pressure liquid chromatography. By comparison with standardized samples of the desired product or reactant, rates of reaction may be quantified.

Alternatively, if the active drug has a cytotoxic effect, the $IC_{50}$s of the active drug, the prodrug, and the combination of the prodrug and the catalytic antibody may be determined as a function of time. The $IC_{50}$ of the combination of the prodrug and the catalytic antibody should approach that of the active drug over time.

These screening protocols allow for the identification of wells containing hybridoma cells producing catalytic monoclonal antibodies. The selected hybridoma cells are then cultured to yield colonies These colonies may be further propagated in vitro or in vivo systems. In the latter case, mice such as syngeneic BALB/C mice are inoculated intraperitoneally with the selected hybridoma cells and produce tumors, generally within two or three weeks. These tumors are accompanied by the production of ascites fluid which contains the desired monoclonal antibodies. The monoclonal antibodies are then separately recovered from the ascites fluid by conventional methods such as ultrafiltration, ultracentrifugation, dialysis and immunoaffinity chromatography.

It will also be possible to prepare polypeptides synthetically which mimic the catalytic antibodies described above. Such synthetic polypeptides may be prepared based on sequencing of the natural polypeptide, either by conventional solid phase synthesis techniques (see, Merrifield (1963) *J. Am. Chem. Soc.*, 85:2149-2156), or by the recombinant polypeptide production techniques described below.

Preparation of Antigens

In the present invention, catalytic antibodies may be elicited with a variety of antigens. In a preferred embodiment, the antigen consists of a carrier molecule, preferably a protein, bound to a hapten by a suitable coupling moiety.

Haptens according to the present invention comprise a reactant, reactive intermediate, or transition state analog, which is involved in the chemical reaction of interest. Usually, the chemical reaction of interest will involve unmasking the prodrug. In a preferred embodiment, the hapten employs a transition state analog which mimics the transition state of an ester hydrolysis reaction. A particularly preferred transition state analog for an ester hydrolysis reaction consists of a derivative of the given ester in which the carboxyl group has been replaced by a phosphonic acid group.

Particularly preferred haptens are a compound of Formula 9 and a compound of Formula 10. These compounds can be produced as described in greater detail below and illustrated in Reaction Schemes 1-4.

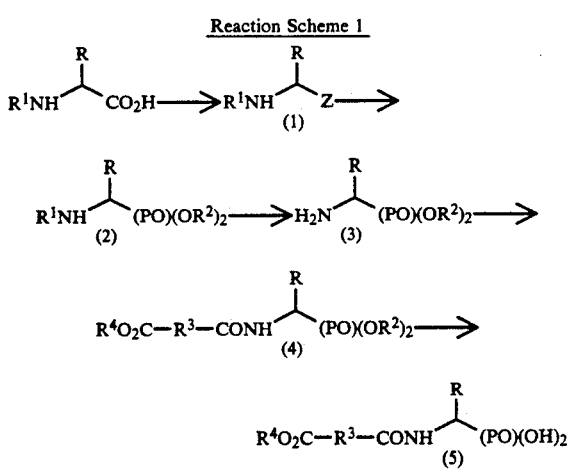

Reaction Scheme 1

Preparation of Compounds of Formula 1, where Z is Acetoxy

Compounds of Formula 1, where Z is acetoxy, can be prepared by the procedure of Corcoran et al. (1990) *Tetrahedron Lett.*, 31:6827–6830, which is incorporated herein by reference. Corcoran describes the oxidative decarboxylation of N-protected amino acids using lead tetraacetate.

Compounds of Formula 1 may be produced from a variety of N-protected amino acids. An amino acid consists of a carbon atom to which is bonded an amino group, a carboxyl group, a hydrogen atom, and a distinctive group referred to as a "side chain". The side chain of the amino acid is designated as group R. The side chains of naturally occurring amino acids are well known in the art and include, for example, hydrogen, alkyl (e.g., as in glycine, alanine, valine, leucine, isoleucine, proline,), substituted alkyl (e.g., as in serine, cysteine, aspartic acid, asparagine, arginine, and lysine), arylalkyl (e.g., as in phenylalanine, histidine, and tryptophan), substituted arylalkyl (e.g., as in tyrosine and thyroxine), and heteroaryl (e.g., as in histidine). See, e.g., Harper et al. (1977) *Review of Physiological Chemistry*. 16th Ed., Lange Medical Publications, pp. 21–24.

In addition to naturally occurring side chains, the amino acids used in the present invention may possess synthetic side chains. Synthetic side chain refers to a side chain in which one or more of the moieties of the naturally occurring side chain is replaced by one or more different moieties. For example, a synthetic side chain may comprise an isostere in which the differing moiety of the synthetic side chain substantially corresponds to the naturally occurring moiety.

Preferred R groups include alkyl and substituted arylalkyl. A particularly preferred substituted arylalkyl group is substituted benzyl such as 4-hydroxybenzyl. In the most preferred embodiment, R is isopropyl.

Naturally occurring and synthetic side chains may contain sensitive functionality, such as hydroxy, mercapto or carboxy groups. One skilled in the art will appreciate that these sensitive groups may have to be protected in order to accomplish the desired reaction sequences. For example, side chains containing a hydroxy group may be glycosylated, phosphorylated, sulphonylated, or otherwise protected. Protection and deprotection techniques are well known in the art. See, e.g., Greene et al. supra.

In order to prepare compounds of Formula 1, the amino group of the amino acid must be protected. One skilled in the art will appreciate that a variety of terminal amino protecting group may be used. The terminal amino protecting group corresponds to the group $R^1$ in a compound of Formula 1. Examples of terminal amino protecting groups may be found in Greene et al., supra, and include carbamates, amides, N-alkyl groups, N-aryl groups, etc. A preferred amino protecting group is the carbobenzyloxy group.

A preferred N-protected amino acid is N-(carbobenzyloxy)-L-valine, which may be purchased from Aldrich Chemical Company, Milwaukee Wisconsin.

Preparation of Compounds of Formula 1, where Z is a Halogen

Compounds of Formula 1, where Z is either iodo, bromo, or chloro, can be prepared through the treatment of an N-protected amino acid with lead tetraacetate and halide ions, preferably iodine, bromide, and chloride. This general procedure is reported in Kochi (1965) *J. Am. Chem. Soc.* 87:2500. A review of this reaction can be found in Sheldon and Kochi (1972) *Org. React.* 19:279–421. Alternatively, compounds of Formula 1, where Z is either iodo, bromo, or chloro can be prepared from an N-protected amino acid using the procedures outlined in March (1985) *Advanced Organic Chemistry* 3rd Ed., John Wiley & Sons: New York, pp. 654–655, which is incorporated herein by reference.

Preparation of Compounds of Formula 2

Compounds of Formula 2 can be prepared through the reaction of a compound of Formula 1, where Z is acetoxy or halo, with a trialkylphosphite. See Corcoran supra; see also, Seebach et al. (1989) *Helv. Chim. Acta*, 72:401. A review of this general reaction can be found in Arbuzov (1964) *Pure Appl. Chem.* 9:307–335. The $R^2$ group of compounds of Formula 2 designates the alkyl group of the trialkylphosphite. Preferably, $R^2$ is a lower alkyl. Most preferably, $R^2$ is methyl.

In a preferred embodiment, a compound of Formula 1, where Z is acetoxy, is treated with trimethylphosphite in the presence of titanium tetrachloride to produce a compound of Formula 2 where $R^2$ is methyl.

To a solution of a compound of Formula 1, preferably 1-acetoxy-1-N-(benzyloxycarbonyl)amino-2-methylpropane, in a polar aprotic solvent, such as methylene chloride, under an inert atmosphere is added a trialkylphosphite, preferably trimethylphosphite. The mixture is cooled, preferably to $-78°$ C. A dilute solution, preferably 1 M, of titanium tetrachloride in a polar aprotic solvent, such as methylene chloride, is slowly added to the solution of a compound of Formula 1. The reaction is allowed to stir at room temperature until the reaction is complete. The product, a compound of formula 2, preferably dimethyl [1-(N-benzyloxycarbonyl)amino]-2-methylpropyl]phosphonate, may be isolated and purified by conventional means.

Preparation of Compounds of Formula 3

Compounds of Formula 3 are produced by the deprotection of compounds of Formula 2. One skilled in the art will appreciate that a variety of reagents and conditions may be used to remove the terminal amino protecting group. The choice of reagents and conditions will depend, in part, on the protecting group used. In a preferred embodiment, the N-benzyloxycarbonyl protecting group is removed with hydrogen and palladium on activated charcoal.

To a solution of a compound of formula 2, preferably dimethyl [1-(N-benzyloxycarbonyl)amino]-2-methylpropyl]phosphonate, in a polar protic solvent, such as ethanol, is added palladium on activated charcoal under positive hydrogen pressure. After the reaction is complete, the mixture is filtered and concentrated under reduced pressure to yield a compound of formula 3, preferably dimethyl (1-amino-2-methylpropyl)phosphonate.

Preparation of Compounds of Formula 4

A compound of formula 4 is produced through the reaction of a compound of formula 3 with a carboalkoxyalkyl halide in the presence of a tertiary amine. In a preferred embodiment, the amide is formed using carbomethoxypropionyl chloride, diisopropylethylamine and dimethylaminopyridine.

The $R^3$ group in a compound of Formula 4 corresponds to the alkyl group of the carboalkoxyalkyl halide. The $R^3$ group may be unsubstituted or substituted with non-interfering substituents. Preferably, $R^3$ will comprise a straight chain alkyl group of 0–10 carbons. A particularly preferred $R^3$ group is $-(CH_2)_2$. The $R^4$ group designates the alkyl component of the alkoxy group. Preferably, $R^4$ will be a lower alkyl, and most preferably, $R^4$ group is methyl.

To a solution of a compound of formula 3, preferably dimethyl (1-amino-2-methylpropyl)phosphonate, in an anhydrous polar aprotic solvent, preferably pyridine, is added a tertiary amine, preferably a mixture of tertiary amines, and most preferably, a mixture of diisopropylethylamine and dimethylaminopyridine. The mixture is cooled, preferably to 0° C, and a carboalkoxyalkyl halide, preferably carbomethoxypropionyl chloride is added. The reaction is allowed to stir until the reaction is complete. The product, a compound of Formula 4, preferably dimethyl [1-[N-(3-carbomethoxypropionyl)amino]-2-methylpropyl]phosphonate, may be isolated and purified by conventional means.

Preparation of Compounds of Formula 5

A compound of Formula 5 is produced via the conversion of the phosphonate group of a compound of Formula 4 to the corresponding phosphonic acid. Preferably, this reaction is accomplished using trimethylsilyl bromide.

To a solution of a compound of formula 4, preferably dimethyl [1-[N-(3-carbomethoxypropionyl)amino]-2-methylpropyl]phosphonate, in an anhydrous polar aprotic solvent, such as methylene chloride, under an inert atmosphere, such as argon, is added trimethylsilyl bromide. The reaction is allowed to stir until complete. The product, a compound of formula 5, preferably [1-[N-(3-carbomethoxypropionyl)amino]-2-methylpropyl]phosphonic acid, may be isolated and purified by conventional means.

Preparation of Compounds of Formula 6

Compounds of Formula 6 are prepared by coupling an active drug to the phosphonic acid group of a compound of Formula 5. Active drugs which contain more than one potential coupling site can be transformed to block the extraneous coupling sites. This transformation can be accomplished through a variety of means which will depend on the coupling sites which must be blocked. For example, a preferred active drug is 2'-deoxy-5-fluorouridine which possesses both a primary and a secondary hydroxyl. It would be desirable to couple the primary hydroxyl to the phosphonic acid group. Thus, the secondary hydroxyl should be protected.

In a preferred embodiment, the primary hydroxyl is first protected, preferably as its dimethoxytrityl (DMT) ether. The secondary hydroxyl is then protected, preferably as its t-butyldimethylsilyl (TBDMS) ether. Finally, the primary hydroxyl protecting group is removed to yield a compound of Formula 6. Compounds of Formula 6 can be produced as described in greater detail below and illustrated in Reaction Scheme 2. A skilled artisan will appreciate that any sequence which allows for the selective protection of a secondary hydroxyl in the presence of a primary hydroxyl may be used.

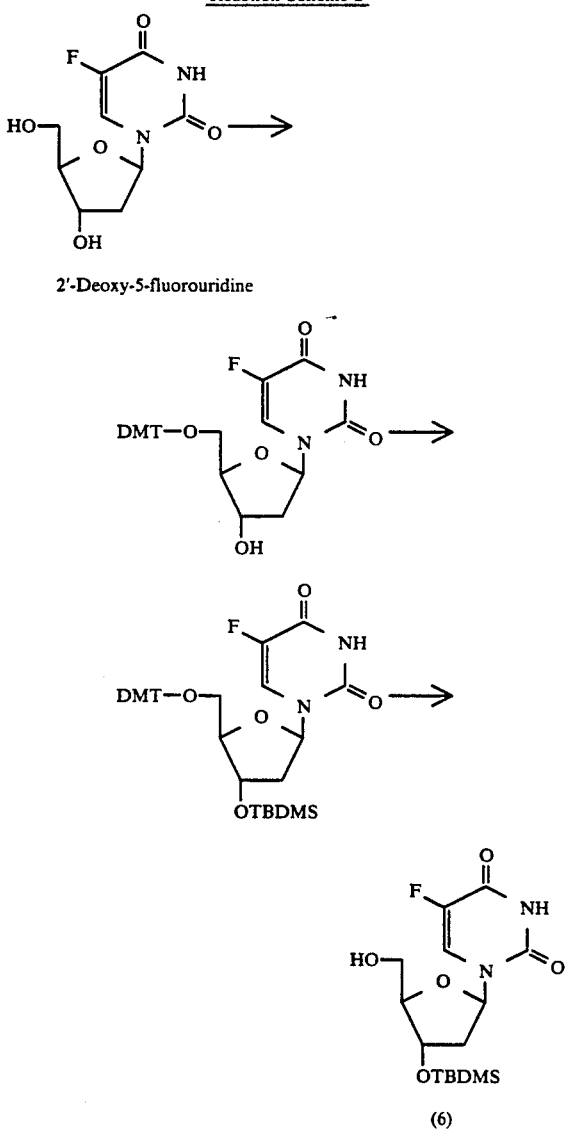

In a preferred embodiment, 2'-deoxy-5-fluorouridine, dimethoxytrityl chloride, and an amine base, preferably a mixture of triethylamine and 4-dimethylaminopyridine, are dissolved in an anhydrous polar, aprotic solvent, preferably pyridine. The reaction is allowed to stir until complete and is then quenched. The mixture is extracted with a polar aprotic solvent such as diethyl ether. The combined organic phases are washed, dried, filtered, and concentrated under reduced pressure.

The resulting foam is dissolved in an anhydrous polar, aprotic solvent, preferably acetonitrile. To this solution is added t-butyldimethylsilyl chloride and imidazole. The reaction is allowed to stir until complete, and is then concentrated under reduced pressure. The mixture is partitioned between water and a polar, aprotic solvent. The aqueous phase is extracted with a polar, aprotic solvent such as ether. The combined organic phases are washed, dried, filtered, and concentrated under reduced pressure.

The resulting compound is dissolved in a solution of a weak acid in a polar aprotic solvent, preferably a 3% solution of trichloroacetic acid in methylene chloride. The reaction is allowed to stir until complete and is then washed, dried, filtered, and concentrated under reduced pressure to yield a compound of Formula 6, preferably 2′-deoxy-3′-O-(t-butyldimethylsilyl)-5-fluorouridine, which may be isolated by conventional means.

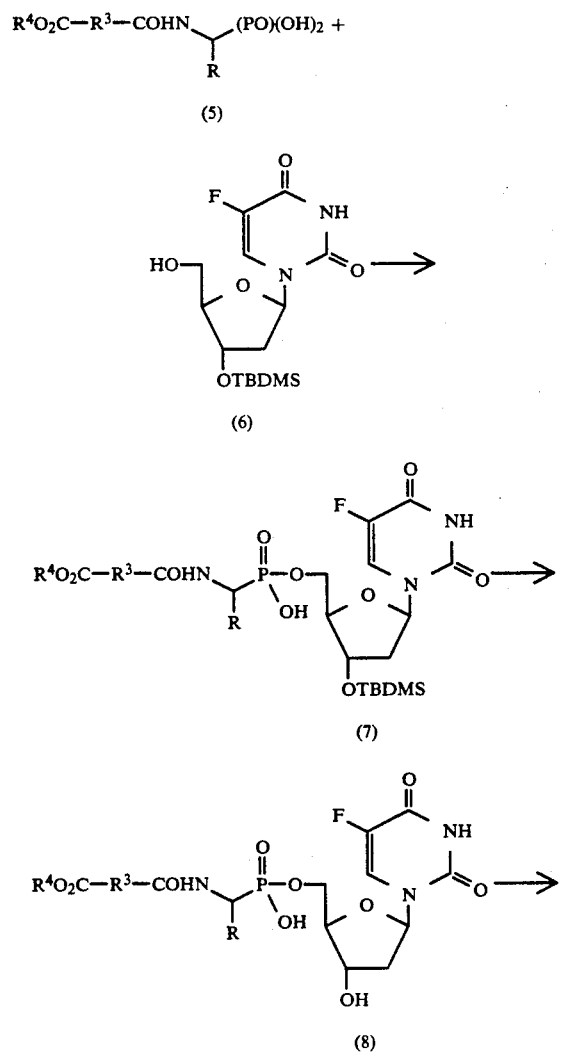

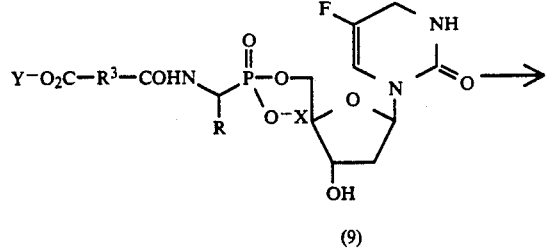

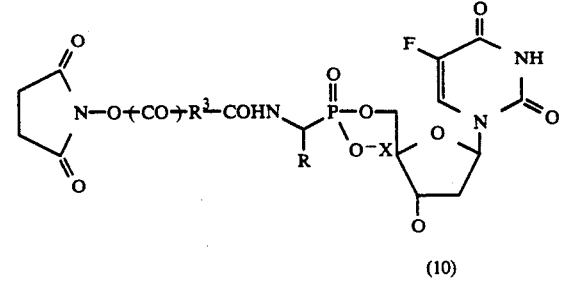

Preparation of Compounds of Formula 7

Compounds of Formula 7 are prepared by joining a compound of Formula 5 with a compound of Formula 6. One skilled in the art will readily appreciate that the manner in which this attachment is accomplished will vary with the compounds being joined. In a preferred embodiment, diisopropylazodicarboxylate and triphenylphosphine are employed to couple a hydroxyl group of a compound of Formula 6 with the phosphonic acid group of a compound of Formula 5. For a review of this general reaction, see Kurihara et al. (1976) *Tetrahedron Lett.*, 2455 and Mitsunobu (1981) *Synthesis*, 1–28.

A compound of Formula 5, preferably [1-[N-(3-carbomethoxypropionyl)amino]-2-methylpropyl]phosphonic acid, a compound of Formula 6, preferably 2′-deoxy-3′-O-(t-butyldimethylsilyl)-5-fluorouridine, and triphenylphosphine are dissolved in an anhydrous polar aprotic solvent, such as tetrahydrofuran, under an inert atmosphere, such as argon. To this solution is added diisopropylazodicarboxylate. The reaction is allowed to stir until complete and is then concentrated under reduced pressure. Isolation by conventional means yields a compound of Formula 7, preferably 2′-deoxy-3′-O-(t-butyldimethylsilyl)-5′-O-[[1-[N -(3-carbomethoxypropionyl)amino]-2-methylpropyl]phosphoryl]-5-fluorouridine.

Preparation of Compounds of Formula 8

Compounds of Formula 8 are prepared through the deprotection of the secondary hydroxyl of compounds of Formula 7. One skilled in the art will appreciate that the choice of reaction conditions will depend on the protecting group, and further, that a variety of reagents and conditions may be used with any one protecting group. In a preferred embodiment, the t-butyldimethylsilyl group may be selectively removed from the secondary hydroxyl with tetrabutylammonium fluoride.

To a solution of a compound of Formula 7, preferably 2′-deoxy-3′-0-(t-butyldimethylsilyl)-5′-O-[[1-[N-(3-carbomethoxypropionyl)amino]-2-methylpropyl]-phosphoryl]-5-fluorouridine, in a polar aprotic solvent, such as tetrahydrofuran, is added tetrabutylammonium fluoride. Additional tetrabutylammonium fluoride may be added as the reaction progresses. Upon completion of the reaction, the mixture is concentrated under reduced pressure to give a compound of Formula 8, preferably, 2'-deoxy-5'-O-[[1-[N-(3-carbomethoxypropionyl)amino]-2-methylpropyl]phosphoryl]-5-fluorouridine, which may be used without further purification.

Preparation of Compounds of Formula 9

Compounds of Formula 9 are formed through ester hydrolysis and salt formation of compounds of Formula 8. One skilled in the art will appreciate that ester hydrolysis and salt formation may occur under a variety of conditions (see, for example, March (1985) *Advanced Organic Chemistry* 3rd Ed., John Wiley & Sons: New York, pp. 348-354, which is incorporated herein by reference). In a preferred embodiment, the ester is hydrolyzed under basic conditions and the alkali metal salt or the organic base salt of the resulting carboxylic acid is produced. Groups X and Y correspond to the counterion of the salt. Generally, X and Y are equivalent. Most preferably, the lithium salt is prepared (i.e., X and Y are lithium).

To a solution of a compound of Formula 8, preferably, 2'-deoxy-3'-O-(t-butyldimethylsilyl)-5'-O-[[1-[N-(3-carbomethoxypropionyl)amino]-2-methylpropyl]-phosphoryl]-5-fluorouridine, in an aqueous polar protic solvent, such as methanol, is added a base, such as potassium carbonate. The reaction is stirred until complete and is then concentrated under reduced pressure. The mixture is purified on a DEAE-sephadex column and is then treated with a cation exchange resin, preferably Dowex-50, to yield a compound of Formula 9, preferably 2'-deoxy-5'-O-[[1-[N-(3-carboxypropionyl)amino]-2-methylpropyl]phosphoryl]-5-fluorouridine, bis-lithium salt.

Preparation of Compounds of Formula 10

Compounds of Formula 10 are prepared by introducing a coupling moiety to a compound of Formula 9. Coupling moieties serve to link the hapten (e.g., a compound of Formula 9) to a carrier molecule.

Coupling moieties are well known in the art (see, e.g., Means et al. (1974) *Chemical Modification of Proteins*, Holden-Day and Thorpe et al. (1982) *Monoclonal Antibodies in Clinical Medicine.* Academic Press, pp. 168-190). For example, coupling moieties may be heterobifunctional in nature, such as, N-succinimidyl 3-(2-pyridyldithio)propionate (SPDP) or the like, to form peptide, amide, ester, thioester, disulfide bridges or other bonds.

One skilled in the art will readily appreciate that the choice of coupling moiety will depend, in part, on the substances being coupled. A particularly preferred coupling moiety is the N-hydroxysuccinimidylcarboxy group which is produced via the reaction of N-hydroxysuccinimide and a carboxylic acid.

To a solution of a compound of Formula 9, preferably 2'-deoxy-5'-O-[[1-[N-(3-carboxypropionyl)amino]-2-methylpropyl]phosphoryl]-5-fluorouridine, bis-lithium salt, in an anhydrous polar aprotic solvent, such as N,N-dimethylformamide, under an inert atmosphere, is added N-hydroxysuccinimide, dicyclohexylcarbodiimide and hydrochloric acid. The reaction is allowed to stir until complete and is then diluted with water. The mixture is centrifuged to remove the dicyclohexylurea. The supernatant is decanted and filtered to give a solution containing a compound of Formula 10, preferably 2'-deoxy-5'-O-[[1-[N-[3-(N-hydroxysuccinimidylcarboxy)propionyl]amino]-2-methylpropyl]phosphoryl]-5-fluorouridine which may be used without further purification.

Protein Conjugation

Haptens may be conjugated to a carrier molecule, preferably a protein, to produce the antigens of the present invention. According to the present invention, the haptens comprise compounds of Formula 9 and compounds of Formula 10. The conjugation reaction may be run under either acidic or basic conditions.

To a cold solution of a protein, preferably BSA or KLH, in a suitable buffer, preferably pH 9.3, 100 mM borate buffer, is added a solution containing a compound of Formula 10, preferably 2'-deoxy-5'-O-[[1-[N-(3-hydroxysuccinimidylcarboxy)propionyl]amino]-2-methylpropyl]phosphoryl]-5-fluorouridine. When the reaction is complete, typically after 24 to 48 hr, the reaction mixtures are dialyzed against PBS-1. The epitope density of the conjugates may be determined using ultra-violet absorbance spectroscopy.

An alternative method of protein conjugation entails the addition of a solution containing a compound of Formula 9, preferably 2'-deoxy-5'-O-[[1-[N-(3-carboxypropionyl)amino]-2-methylpropyl]phosphoryl]-5-fluorouridine, bis-lithium salt, and 1-ethyl-3-(3-dimethylaminopropyll)carbodiimide to a pH 6.5 aqueous solution of a protein, preferably BSA or KLH. When the reaction is complete, the reaction mixtures are dialyzed against PBS-1. The epitope density of the conjugates may be determined using ultra-violet absorbance spectroscopy.

The Linker Region

The targeting moiety is complexed to an activating moiety via a linker region. Besides functioning to keep the two moieties from separating, the linker region functions to ensure that the activating moiety is in the proper conformation to enhance the rate of a chemical reaction when the targeting moiety is bound to the target site. The linker does not significantly decrease the affinity of the targeting moiety for the target site or the rate enhancing properties of the activating moiety.

The linker region may comprise hetero- or homobifunctional crosslinking agents that can form covalent bonds with both the activating moiety and the targeting moiety. See, e.g., Pierce Immunotechnology Catalog and Handbook (1991), pp. E8-39 and Thorpe et al. *Monoclonal Antibodies in Clinical Medicine.* Academic Press, pp. 168-190 (1982). Alternatively, the targeting and activating moieties may be joined as a single polypeptide (chimeric fusion protein) by recombinant DNA methods. See, e.g., for descriptions of immunotoxins consisting of interleukin-2 fused to diphtheria toxin or domain II of Pseudomonas exotoxin, Williams et al. (1987) *Protein Enq.*, 1:493; Siegall et al. (1988) *Proc. Natl. Acad. Sci. USA*, 85:9738. See also, Pastan et al. (1991) *Science*, 254:1173. The linked peptides in the chimeric proteins should be sufficiently flexible and of a length that permits the targeting and activating moieties to assume their appropriate conformation for full activity. Linker regions similar to those used in the production of single-chain antibodies may be suitable for this purpose. See Huston et al. (1988) *Proc. Natl. Acad. Sci. USA.* 85:5879.

Preparation of Site-Directed Catalytic Antibodies

Site-directed catalytic antibodies may be prepared by synthetic and recombinant preparation methods where the polypeptide is produced to have a specific amino acid sequence. These synthetic and recombinant techniques will usually start with an exemplary amino acid sequence which is characteristic of a protein which is known to bind a reactant (i.e., a prodrug) or reactive intermediate with the requisite affinity. Such exemplary amino acid sequences may be derived from enzymes which are known to catalyze the chemical reaction of interest or from antibodies which have been raised against reactants or transition state analogs of the reaction of interest.

For the preparation of larger and/or glycosylated polypeptides, recombinant preparation techniques are usually preferred. Such recombinant techniques involve the expression in cultured cells of recombinant DNA molecules encoding the desired polypeptide amino acid sequence. The DNA sequence may itself be synthetic or alternatively be modified from a natural source, i.e., the gene of an exemplary antibody or enzyme.

Synthetic DNA sequences (polynucleotides) may be synthesized by well-known techniques. For example, short-single stranded DNA fragments may be prepared by the phosphoramidite method described by Beaucage and Carruthers (1981) Tett. Letters, 22:1859–1862. A double-stranded fragment may then be obtained by either synthesizing a complementary strand and annealing the strands together under appropriate conditions or by adding the complementary strand using DNA polymerase with an appropriate primer sequence. Conveniently, automated equipment for preparing the synthetic DNA sequences is available from the suppliers listed above as providing synthetic polypeptide equipment.

Alternatively, the desired DNA sequences may be obtained from a suitable cDNA or genomic library obtained from a cell line expressing the exemplary protein of interest. For example, the gene expressing a monoclonal antibody of interest may be isolated from the hybridoma cell line expressing such antibody. The techniques for isolating antibody genes from hybridoma cell lines are well described in the scientific literature. See, for example, Gearhart et al. (1983) Proc. Natl. Acad. Sci. USA, 80:3439–3443.

The natural or synthetic DNA fragments coding for the desired polypeptide will be incorporated in DNA constructs capable of introduction to and expression in an in vitro cell culture. The DNA constructs may be suitable for replication in a unicellular host, such as yeast or bacteria, but can be intended for introduction into and integration within the genome of cultured mammalian or other eukaryotic cell lines. DNA constructs prepared for introduction into bacteria or yeast will include a replication system recognized by the host, the DNA fragment encoding the polypeptide of interest, transcriptional and translation initiation regulatory sequences joined to the 5'-end of the DNA sequence, and transcriptional and translational regulatory sequences joined at the 3'-end of the DNA sequence. The transcriptional regulatory sequences will include a heterologous promoter which is recognized by the host. Conveniently, available expression vectors which include replication systems and transcriptional and translational regulatory sequences together with an insertion site for the DNA sequence to be expressed may be employed.

Of particular interest to the present invention are expression systems for the Fv and F(ab) regions of an antibody molecule. Such systems are described in Bird et al. (1988) Science, 242:423; Huston et al. (1988) Proc. Natl. Acad. Sci. USA, 85:5879; Skerra and Pluckthun (1988) Science, 240:1028; and Better et al. (1988) Science, 240:1041. Polypeptides comprising these regions retain the binding specificity of the intact antibody from which they are derived, but are substantially smaller and may be produced in a variety of expression hosts, e.g., E. coli, which may offer advantages over the production of intact monoclonal antibodies in hybridoma cell lines.

It will frequently be desirable to produce both the $V_L$ and $V_H$ chains of the Fv region as a single fusion protein joined by an appropriate linker which allows for folding. Such single chain expression systems are described in Bird et al. (1988), supra, and Huston et al. (1988), supra. Alternatively, the $V_L$ and $V_H$ chains may be expressed and subsequently reconstituted under appropriate conditions. Such separate chain expression systems are described in Skerra and Pluckthun (1988) supra, and Bette et al. (1988) supra.

Synthesis of Prodrugs

The site-directed catalytic antibodies of the present invention are administered in conjunction with a prodrug. The prodrug usually will comprise a masked form of the active drug. In a preferred embodiment, the prodrug of the instant invention consists of an active drug which has been masked as the ester of an amino acid. More preferably, the prodrug consists of the D-amino acid ester of the active drug. The D-isomer is preferred because mammalian esterases typically require amino acids to have the L-configuration for activity while D-amino acids are not hydrolyzed (see, for example, Bundgaard, H., ed., (1985) Design of Prodrugs, pp. 93–103, Elsevier Science Publishers: Amsterdam). Thus, the prodrug will be activated only by the administered site-directed catalytic antibody and not by endogenous enzymes.

A variety of amino acids may be used to prepare the prodrugs. The side chain of the amino acid corresponds to the $R^5$ group in the compound of Formula 11. As in compounds of Formula 1, the side chain of the prodrug may be either naturally occurring or synthetic and may comprise hydrogen, alkyl, aryl, heteroaryl, or arylalkyl groups. The side chain of the prodrug (i.e., $R^5$) will typically correspond to the side chain (i.e., R) of the hapten used to generate the activating moiety. A particularly preferred side chain is isopropyl. Thus, a particularly preferred amino acid is D-valine.

The terminal amino group of the amino acid may optionally be protected with an appropriate protecting group. The group $R^6$ in compounds of Formula 11 comprise this terminal amino protecting group or hydrogen. A skilled artisan will appreciate that a variety of terminal amino protecting groups can be used. Examples of terminal amino protecting groups may be found in Greene et al., supra, and include carbamates, amides, N-alkyl groups, N-aryl groups, etc. A particularly preferred terminal amino protecting group is acetyl.

In a preferred embodiment, the prodrug is an amino acid ester of an antimetabolite. Antimetabolites are compounds that interfere in either the biosynthesis, utilization, or metabolic function of normal cellular metabolites. To be successfully selective in the chemotherapy of tumors, an antimetabolite should adversely affect one or more vital metabolic reactions in the tumor without seriously endangering normal tissues. Some of the most successful antimetabolites used in the treatment of cancer are those based on purine or pyrimidine analogs whose activity is dependent on their ability to inhibit DNA or RNA synthesis. One such drug is 2'-deoxy-5-fluorouridine. See *Physicians' Desk Reference*, 46th Ed., (1992), and American Medical Association (1992) *Drug Evaluation Subscriptions*.

2'-Deoxy-5-fluorouridine is a highly toxic drug. It is typically administered by regional intra arterial infusion via a catheter inserted into the arterial blood supply of the tumor. Generally, because of the high systemic toxicity of 2'-deoxy-5-fluorouridine, patients with carcinoma extending beyond an area capable of being infused via a single artery are not candidates for treatment. However, even with direct arterial administration of the drug, toxic effects related to the drug-infused area are usually evident.

According to the present invention, 2'-deoxy-5-fluorouridine can be modified to a prodrug, specifically, an amino acid ester derivative. This prodrug should be substantially less toxic than the active drug. Moreover, the prodrug will be converted to the active form at the target site via the site-directed catalytic antibody. This should decrease the systemic toxic effects of the drug and allow for a wider variety of modes of drug administration.

A particularly preferred prodrug is the D-amino acid ester of 2'-deoxy-5-fluorouridine (i.e., the D-isomer of a compound of Formula 11). Compounds of Formula 11 can be produced as described in greater detail below and illustrated in Reaction Scheme 4.

Reaction Scheme 4

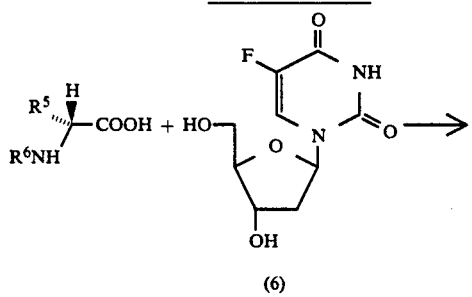

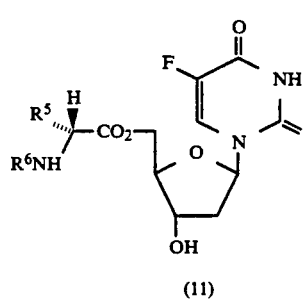

One skilled in the art will readily appreciate that esters can be produced with a variety of conditions and reagents (see, for example, March (1985) *Advanced Organic Chemistry* 3rd Ed., John Wiley & Sons: New York, pp. 348-354). In a preferred embodiment, the ester formation occurs using triphenylphosphine and diisopropylazodicarboxylate. See Kurihara supra and Mitsunobu supra.

To a solution of the active drug, preferably 2'-deoxy-5-fluorouridine, an N-protected amino acid, preferably N-acetyl-D-valine, and triphenylphosphine in an anhydrous polar aprotic solvent is added diisopropylazodicarboxylate. Upon completion of the reaction, the mixture is concentrated under reduced pressure. The prodrug, preferably a compound of Formula 11, most preferably, 2'-deoxy-5'-O-(N-acetyl-D-valinyl)-5-fluorouridine, may be isolated by conventional means.

Preferably, the site-directed catalytic antibody and the prodrug are administered sequentially to the host. Sequential treatment involves initial administration of the site-directed catalytic antibody. The prodrug is administered only after the site-directed catalytic antibody has had sufficient time to localize at the target site and the unlocalized site-directed catalytic antibody has been cleared from the host. Typically, the period between treatment with the site-directed catalytic antibody and treatment with the prodrug will be about 24 to 72 hours.

Administration of the prodrug and site-directed catalytic antibody described herein can be via any of the accepted modes of administration for therapeutic agents. These methods include oral, parenteral, transdermal, subcutaneous and other systemic modes.

Depending on the intended mode, the compositions may be in the form of solid, semi-solid or liquid dosage forms, such as, for example, tablets, suppositories, pills, capsules, powders, liquid solutions or suspensions, liposomes, suppositories, injectable and infusable solutions, or the like, preferably in unit dosage forms suitable for single administration of precise dosages. The preferred form depends on the intended mode of administration and therapeutic application. The compositions may also include conventional pharmaceutical excipient, other medicinal agents, pharmaceutical agents, carriers, adjuvants, diluents, etc. which are known to those of skill in the art. See, e.g., *Reminqton's Pharmaceutical Sciences*, Mack Publishing Co.: Easton, Pa., 17th Ed. (1985).

The invention will be more fully described and understood with reference to the following illustrative examples.

EXPERIMENTAL

Example 1

1.1 A Compound of Formula 2 where R is Isopropyl, Dimethyl (1-(N-(Benzyoxvcarbony)amino-2-methylpropyl]phosphonate To a suspension of lead tetraacetate (6.537 g, 14.7 mmol) in dry N,N-dimethylformamide (20 ml) under argon at 0° C., was added N-(carbobenzyloxy)-L-valine (3.082 g, 12 3 mmol). After 1 hour cooling was stopped and stirring continued an additional 3 hours at room temperature. The reaction was quenched with saturated NaHCO3 (100 ml) and extracted with ethyl acetate (50 ml×1 25 ml x 3). The organic layers were combined, washed with saturated NaHCO3 (25 ml), 5% NaHCO3 (25 ml), H2O (25 ml), and brine (25 ml), then dried over MgSO4, filtered, and concentrated under vacuum.

The acetate, isolated as an oil, was immediately dissolved in dry methylene chloride (20 ml) under argon, trimethylphosphite (2.2 ml, 18.7 mmol) was added and the mixture was cooled (−78° C.) before slowly adding TiCl$_4$ (15 mmol), as a 1M solution in methylene chloride. Cooling was stopped and stirring continued at room temperature for 12 hours. The reaction mixture was then cooled to 0° C. and quenched with Na$_2$CO$_3$10-H$_2$O (35 g, 120 mmol). Cooling was stopped and stirring continued at room temperature for 30 minutes. The mixture was diluted with H$_2$O (100 ml) and extracted with CH$_2$Cl$_2$ (25 ml×4). The organic phase was washed with H$_2$O (25 ml) and brine (25 ml×2), dried over MgSO$_4$, filtered, then concentrated under vacuum, yielding 3.855 g (12.24 mmol, quantitative yield) of a compound of formula 2, where R is isopropyl, dimethyl [1-[N-(benzyloxycarbonyl)amino]-2-methylpropyl]-phosphonate, as a colorless oil.

1.2 A Compound of Formula 3, where R is Isopropyl, Dimethyl (1-Amino-2-methypropl)phosphonate To a compound of Formula 2, where R is isopropyl, dimethyl [1-[N-(benzyloxycarbonyl)amino]-2-methylpropyl]phosphonate (0.231 g, 0.73 mmol), dissolved in ethanol (5 ml) was added palladium on activated charcoal (39 mg), under positive hydrogen pressure. After 4 hours the mixture was filtered through celite and washed with methanol. The filtrate was collected and concentrated under vacuum, yielding 0.133 g (0.73 mmol, quantitative) of a compound of Formula 3, where R is isopropyl, dimethyl (1-amino-2-methylpropyl)phosphonate as a colorless oil.

1.3 A Compound of Formula 4, where R is Isopropyl, Dimethyl 1-N-(3-Carbomethoxyprooionyl)amino[-2-methyl-propyl]phosphonate To a compound of Formula 3, where R is isopropyl, dimethyl (1-amino-2-methylpropyl)phosphonate (0.184 g, 1.02 mmol) dissolved in dry pyridine (5 ml) under argon, was added diisopropylethylamine (0.34 ml, 2.04 mmol) and dimethylaminopyridine (64 mg, 0.52 mmol). The mixture was cooled to 0° C., and carbomethoxypropionyl chloride (0.19 ml, 1.54 mmol) was added. After 2 hours the reaction was quenched with H$_2$O and concentrated under vacuum. The resulting golden-brown oil was diluted with ether (50 ml) and washed with H$_2$O (10 ml×5). The aqueous phase was acidified to pH 2 with concentrated HCl and extracted with ethyl acetate (15 ml×5). The ethyl acetate phase was washed with brine (15 ml), dried over MgSO$_4$, filtered, and concentrated under vacuum. Silica gel chromatography (elution with 7.5% methanol/CH$_2$Cl$_2$) yielded 0.103 g (0.35 mmol, 34%) of a compound of Formula 4, where R is isopropyl, dimethyl [1-[N-(3-carbomethoxypropionyl)amino]-2-methylpropyl]phosphonate.

1,4 A Compound of Formula 5, where R is Isopropyl, [1-[N-(3-Carbomethoxypropionyl)amino]-2-methylpropyl]phosphonic acid To a compound of Formula 4, where R is isopropyl, dimethyl [1-[N-(3-carbomethoxypropionyl)amino]-2-methylpropyl]phosphonate (103 mg, 0.35 mmol) dissolved in dry methylene chloride (3 ml) under argon, was added trimethylsilyl bromide (0.23 ml, 1.74 mmol). After 1 hour the reaction was quenched with methanol, then triturated with acetic acid (5 ml x 3), methanol (5 ml×3), and ether (1 ml×2). Concentration under vacuum yielded 93 mg (0.35 mmol, quantitative) of a compound of Formula 5, where R is isopropyl, [1-[N-(3-carbomethoxypropionyl)amino]-2-methylpropyl]phosphonic acid as a cream colored solid.

1.5 A Compound of Formula 6, 2'-Deoxy-3'-O-(t-butyldimethylsilyl)-5-fluorouridine 2'-Deoxy-5-fluorouridine (0.492 g, 2.00 mmol), dimethoxytrityl chloride (0.956 g, 2.82 mmol), triethylamine (0.42 ml, 3.01 mmol), and 4-dimethylaminopyridine (0.053 g, 0.42 mmol) were dissolved in dry pyridine (15 ml). After 14 hours the reaction was quenched with H$_2$O (25 ml) then extracted with ether (25 ml×5). The organic phase was washed with brine (25 ml), dried over MgSO$_4$, filtered, and concentrated under vacuum. To a solution of the resulting foam in dry acetonitrile (50 ml), was added t-butyldimethylsilyl chloride (0.733 g, 5.12 mmol) and imidazole (0.696 g, 1.02 mmol). After 22 hours the mixture was concentrated under vacuum and partitioned between H$_2$O (50 ml) and ether (50 ml). The aqueous phase was extracted with additional ether (25 ml ×3). The organic phase was washed with brine (50 ml), dried over MgSO$_4$, filtered, and concentrated under vacuum. The resulting foam was dissolved in a 3% solution of trichloroacetic acid in methylene chloride (75 ml). After 45 minutes the reaction mixture was washed with saturated NaHCO$_3$ (25 ml×3) and brine (25 ml), dried over MgSO$_4$, filtered, and concentrated under vacuum. Silica gel chromatography yielded 0.247 g (0.68 mmol, 34%) of a compound of Formula 6, 2'-deoxy-3'-O-(t-butyldimethylsilyl)-5-fluorouridine; as a peach colored solid.

1.6 A Compound of Formula 7, where R is Isopropyl, 2'-Deoxy-3'-O-(t-butyldimethylsilyl)-5'-O-[[1-[N-(3-carbomethoxypropionyl)amino[-2-methylpropyl]-phosphoryl]-5-fluorouridine A compound of Formula 5, where R is isopropyl, [1-[N-(3-carbomethoxypropionyl)amino[-2-methylpropyl]phosphonic acid (93 mg, 349 μmol), a compound of Formula 6, 2'-deoxy-3'-O-(t-butyldimethylsilyl)-5-fluorouridine (71 mg, 197 μmol), and triphenylphosphine (80 mg, 305 μmol) were dissolved in dry tetrahydrofuran (5 ml) under argon. To this solution, was added diisopropylazodicarboxylate (60 μl, 305 μmol). After 18 hours the mixture was concentrated under vacuum. Silica gel chromatography yielded 88 mg (144 μmol, 73%) of a compound of Formula 7, where R is isopropyl, 2'-deoxy-3'-O-(t-butyldimethylsilyl)-5'-O-[[1-[N-(3-carbomethoxypropionyl)amino]-2-methylpropyl]phosphoryl]-5-fluororuridine.

1.7 A Compound of Formula 9, where R is Isopropyl, 2'-Deoxy-5'-O-[[1-[N-(3-carboxypropionyl)amino]-2-methylpropyl]phosphoryl]-5-fluorouridine, bis-lithium salt To a compound of Formula 7, where R is iospropyl, 2'-deoxy-3'-O-(t-butyldimethylsilyl)-5'-O-[[1-[N-(3-carbomethoxypropionyl)amino[-2-methylpropyl[-phosphoryl]-5-fluorouridine, (86 mg, 141 μmol) dissolved in tetrahydrofuran (10 ml) was added tetrabutylammonium fluoride (70 μmol). Additional tetrabutylammonium fluoride (140 μmol) was added after 3 hours. After 48 hours the reaction mixture was concentrated under vacuum and dissolved in wet methanol (15 ml). To this solution was added potassium carbonate (54 mg, 391 μmol). After stirring at room temperature for 43 hours the reaction mixture was concentrated under vacuum. Purification on a DEAE-sephadex column yielded 52 mg of the bistriethylammonium salt, which was treated with Dowex-50 cation exchange resin resulting in 45 mg (91μmol, 65%) of a compound of Formula 9, where R is isopropyl, 2'-deoxy-5'-O-[[1-[N-(3-carboxypropionyl)amino]-2-methylpropyl]phosphoryl]-5-fluorouridine, bis-lithium salt, as a colorless solid.

1 8 A Compound of Formula 10, where R is Isopropyl,

2'-Deoxy-5'-O-[[[1-[N-[3-(N-hydroxvsuccinimidylcarboxy)propionyl]amino]-2-methylpropyl]phosphoryl]-5-fluororuridine To a compound of Formula 9, where R is isopropyl, 2'-deoxy-5'-O-[[1-[N-(3-carboxypropionyl)amino]-2-methylpropyl]phosphoryl]-5-fluorouridine, bis-lithium salt, (10 mg, 200 μmol) dissolved in dry N,N-dimethylformamide (200 μl) under argon, was added N-hydroxysuccinimide (7 mg, 61 μmol), dicyclohexylcarbodiimide (27 mg, 131 μmol), and HCl (2 μl, 24μmol). After stirring for 29 hours at room temperature the reaction mixture was diluted with H$_2$O (1 ml) and centrifuged to pellet the DCU. The supernatant was decanted and filtered through a 0.45 μm filter. The resulting solution was used directly for protein conjugation.

Example 2

Protein Conjugation 2.1 Method A

BSA (71 mg) and KLH (63 mg) were added to pH 9.3, 100 mM borate buffer (3 ml), centrifuged (3600 rpm, 10° C.), the supernatants isolated and further diluted with buffer (2 ml). The solution containing compound 10 (300 μl) was added to aliquots of each protein (2 ml) over a 15 minute period at 4° C. After 48 hours the reaction mixtures were dialyzed against PBS-1 (1 1×3). An ultra-violet absorbance assay was used to determine the epitope density of the conjugates, 1 for KLH, and 5 for BSA.

2.2 Method B

BSA (61 mg) and KLH (52 mg) were added to H$_2$O (5 ml) and the pH adjusted to 6.5 with dilute HCl. The protein mixtures were centrifuged (3600 rpm, 10° C.), and the supernatants isolated. Aliquots (2 ml) were treated with a solution of a compound of Formula 9 (5 mg, 10 μmol) and 1-ethyl-3-(3-dimethylaminopropyl)-carbodiimide (EDC, 6 mg, 31 μmol) and the pH readjusted to 6.5. After 2 hours, additional EDC (5 mg, 26 μmol) was added, and the pH was adjusted to 6.5. After 24 hours at room temperature the reaction mixtures were dialyzed against PBS-1 (750 ml×3). The ultra-violet absorbance assay indicated epitope densities of 6 for BSA, and 8 for KLH.

Example 3

Preparation of Prodrugs 3.1 The D-Isomer of a Compound of Formula 11, where R is Isopropyl, 2'-Deoxy-5'-O-(N-acetyl-D-valinyl)-5-fluorouridine Diisopropylazodicarboxylate (250 μl, 1.27 mmol) was slowly added to a mixture of 2-deoxy-5-fluorouridine (0.206 g, 837 μmol), N-acetyl-D-valine (0.199 g, 1.25 mmol), and triphenylphosphine (0.327 g, 1.25 mmol) in dry tetrahydrofuran (8 ml). After 3 hours the reaction mixture was concentrated under vacuum. Silica gel chromatography (elution with 8% methanol/CH$_2$Cl$_2$) yielded 0.115 g (296 μmol, 36%) of a compound of Formula 11, where R is isopropyl, 2'-deoxy-5'-O-(N-acetyl-D-valinyl)-5-fluorouridine as a colorless solid.

3.2 The L-Isomer of a Compound of Formula 11, where R is Isopropyl,

2'-Deoxy-5'-O-(N-acetyl-L-valinyl)-5-fluorouridine

Diisopropylazodicarboxylate (170 μl, 863 μmol) was slowly added to a mixture of 2'-deoxy-5-fluorouridine (0.141 g, 573 μmol), N-acetyl-L-valine (0.141 g, 886 μmol), and triphenylphosphine (0.221 g, 843 μmol) in dry tetrahydrofuran (6 ml). After 3 hours the reaction mixture was concentrated under vacuum. Silica gel chromatography (elution with 7.5% methanol/CH$_2$CL$_2$) yielded 0.100 g (258 μmol, 45%) of a compound of Formula 11, where R is isopropyl, 2'-deoxy-5'-O-(N-acetyl-L-valinyl)-5-fluorouridine, as a colorless solid.

Example 4

Plasma Stability Studies

The stability of the D- and L-isomers of a compound of Formula 11, where R is isopropyl, in both mouse and human plasma was determined with an HPLC assay of solutions containing plasma (90 μl) and 1 mM of a compound of Formula 11 (10 μl of a 10 mM aqueous solution, 100 nmol), incubated at 37° C. In mouse plasma the L-isomer of a compound of Formula 11, where R is isopropyl, had a half-life of 44 hours, and the D-isomer of a compound of Formula 11, where R is isopropyl, 67 hours. In human plasma, the L-isomer of a compound of Formula 11, where R is isopropyl, had a half-life of 23 hours, while the D-isomer of a compound of Formula 11, where R is isopropyl, was stable through 48 hours.

Example 5

Preparation and Screening or Catalytic Antibodies

Mice are immunized with the KLH conjugate of Example 2. Monoclonal IgG antibodies that react with the BSA conjugate are generated by standard procedures and are propagated as ascites tumors in syngenic mice. The antibodies are purified by affinity chromatography on Protein A (Affi-Gel). Stock solutions (50 μM) in Tris buffer, pH=7.5, are prepared.

Antibodies (10 μM) are assayed for their ability to catalyze the hydrolysis of prodrug 2'-deoxy-5'-O-(N-acetyl-D-valinyl)-5-fluorouridine (a compound of formula 11) to 5-fluorouridine in 20 mM Tris buffer, pH=7.5, and 100 mM sodium chloride at 37° C. In all assays, formation of 5-fluorouridine is monitored by HPLC analysis (Rainin C18 reverse phase column 4.6 ×150 mm, eluting with 50 mM aqueous triethylamine-sodium acetate, pH=7.5/acetonitrile) with 4-nitrophenol as an internal standard. The rate of hydrolysis for 2'-deoxy-5'-O-(N-acetyl-D-valinyl)-5-fluorouridine (a compound of formula 11) is found to be enhanced above the background uncatalyzed rate by several antibodies. These rates are fitted to the Michaelis-Menten expression to provide kinetic constants k$_{cat}$, and K$_M$ for the catalytic antibodies as described in Stryer (1988) *Biochemistry*, 3rd Ed., W.H. Freeman and Co., New York, pp. 187–191, which is incorporated herein by reference.

An alternative procedure for screening the catalytic antibodies is based on a comparison of the IC$_{50}$s of the active drug, the prodrug, and the prodrug in combination with the catalytic antibody. The active drug, the prodrug, and the prodrug in combination with the catalytic antibody are incubated with either HeLa or L1210 cells. The IC$_{50}$ for each are then determined using an assay based on the conversion of a tetrazolium salt into a blue formazan product that is easily detected using an ELISA plate reader. See, e.g., Mosmann (1983) *J. Immunol. Meth.*, 65:55–63; Tada et al. (1986) *J. Immunol. Meth.*, 93:157–165; and Hansen et al. (1989) *J. Immunol. Meth.*, 119:203–210, which are incorporated herein by reference. The IC$_{50}$ determinations are repeated over a period of time.

The IC$_{50}$ of the prodrug will be high compared to that of the active drug. The IC$_{50}$ of the combination of the prodrug and the site-directed catalytic antibody should approach that of the drug over time.

Example 6

Preparation of Catalytic Antibody Fragments

6.1 Preparation of Fab'

The Fab' fragment is prepared by the method of Inbar et al. (1971) *J. of Biol. Chem.*, 246:6272, which is incorporated herein by reference.

One gram of catalytic antibody as derived from Example 5, in eluting buffer (0.15M NaCl, 0.01M sodium phosphate buffer at pH 7.4) is adjusted to pH 4.7 by the addition of 0.5M sodium acetate buffer, pH 4.5, and then 10 mg pepsin (in 1 ml of 0.005M sodium acetate, pH 4.5) is added. The mixture is incubated for six hours at 37 C and then centrifuged to remove precipitate. The supernatant is adjusted to pH 8 and applied to a column (3×14 cm) of hapten (preferably, a compound of formula 9) covalently coupled to sepharose. The Fab' fragment is eluted with 0.1M citrate buffer, pH=3.0 and is immediately neutralized with 1M Tris to pH=7.5. Activity of the purified Fab' is assayed as in Example 5.

6.2 Preparation of Fv Fragment

The Fv fragment is prepared from the catalytic antibody of Example 5 or from an Fab' fragment from Example 6.1. Either the antibody or the Fab' fragment is cleaved to the Fv fragment by the method of Hochman et al. (1973) *Biochemistry*, 12:1130, which is incorporated herein by reference.

The Fab' fragment or antibody (10 mg/ml in 0.15 M NaCl, 0.01M sodium phosphate buffer at pH 7.4) is adjusted to pH 3.8 by the addition of 1M sodium acetate, pH 3.7. To the turbid protein solution, is added pepsin (10 mg/ml in 0.01M sodium acetate, pH 3.7) to give a weight ratio of 1:100 of enzyme to Fab'. After four hours at 37 C the digestion is terminated by adjusting the pH to 7.0 with 2M Tris-HCl, pH 8.2. Precipitate not dissolved by the rise in pH is removed by centrifugation. The supernatant is applied to a column of hapten (preferably, a compound of formula 9) covalently coupled to sepharose. The column is eluted with 0.1M citrate buffer, pH =3.0 and resulting solution is immediately neutralized with 1 M Tris to pH =7.5. The desired fraction is collected, concentrated by vacuum dialysis, and applied to a Sephadex G-75 column, to separate Fv from undigested Fab' by the method of Hochman et al. (1972) *Proc. Natl. Acad. Sci. USA*, 69:2659, which is incorporated herein by reference. Catalytic activity of the purified Fv is assayed as in example 5.

6.3 Separation of Fv into V$_L$ and V$_H$ Fragments

The heterodimer Fv is separated into its H- and L-chain derived components by the method of Hochman et al. supra. Briefly Fv is chromatographed in 8M urea at pH 9.0 on DEAE-cellulose.

Alternatively, to about 2 mg Fv is added, NaCl to 0.15M, and mercaptoethanol to 0.2M in a final volume of 5 ml of 50 mM Tris-HCl, pH 7.3. The mixture is incubated at 24 C for 3 hrs. with shaking. To the mixture is then added 2 ml of 0.5M iodoacetamide. Tris-HCl (1M) is then added to bring the pH to 7.5. The mixture is then incubated for 15 min at 24 C with shaking. The sample is then concentrated to reduce the volume to about 1 ml on a 10 kD ultrafilter.

The resulting concentrated sample is chromatographed on Superrose-12 in buffer (0.1M glycine-HCl, 0.05M Tris-HCl, pH 8.0 containing 0.025% Tween 20). The protein peaks from the Superose-12 are analyzed by SDS-PAGE.

The H- and L-chain fractions produced by either method are distinguished using standard immunoblotting methods. Gels are blotted on nitrocellulose membranes. The membranes are incubated with anti H-chain (Accurate) and anti L-chain (kappa/lambda) antibodies. The membranes are washed with buffer, incubated with antirabbit IgG conjugated with peroxidase, washed and then stained with diaminobenzidine and hydrogen peroxide.

Example 7

Preparation of Site-Directed Catalytic Antibodies

Anti-Ly-2.1 (IgG$_{2a}$) reactive with the murine Ly-2.1+$^{ve}$ thymoma cell line E3 is purified from ascites fluid as described in Hogarth et al. (1982) *Immunology*, 46:135–155. Anti-Ly-2.1 (1.5 mg/ml) in 20 mM borate buffer (pH=8.0) is treated with 6-[3-(2pyridyldithio)-propionamido]hexanoate (Pierce Chemical Co., Rockford, Ill. (10 μM) and the derivatized targetting antibody is purified by gel filtration on G-25 sephadex. (Fab')$_2$ (1.5 mg/ml in phosphate buffered saline pH=7.0) from an isolated catalytic antibody is treated with dithiothreitol (DTT) (10 mM). The reduced Fab' fragment is purified by FPLC on a Superose 12 column and immediately reacted with the derivatized Anti-Ly-2.1 antibody. Purification of the site-directed catalytic antibody conjugate is by FPLC on Superose 12.

Example 8

In Vitro Catalytic Activity Assay

In vitro antitumor activity of the prodrug 2'-deoxy-5'-O-(N-acetyl-D-valinyl)-5-fluorourine (a compound of formula 11) against the E3 cell line as potentiated by the site-directed catalytic antibody is assayed as described in Goerlach et al. (1991) *Bioconjugate Chem.*, 96–101, which is incorporated herein by reference.

Example 9

In Vivo Catalytic Activity Assay

The conversion of the prodrug to the active drug by the site-directed catalytic antibody in the presence of target cells results in inhibition of DNA synthesis and cell-killing. In vivo activity is assayed as described in Geran et al. (1972) *Cancer Chemother. Rep.* 3, (3):7, which is incorporated herein by reference.

The disclosures of all articles and references, including patents, are incorporated herein by reference.

The above description is intended to be illustrative and not restrictive. Many embodiments will be apparent to those of skill in the art upon reviewing the above

We claim:

1. A compound having the formula:

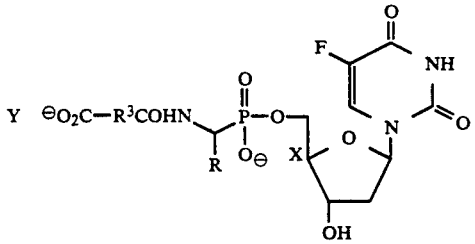

in which R is selected from the group consisting hydrogen, methyl, isopropyl, isobutyl, sec-butyl, and 4-hydroxybenzyl; X and Y are independently selected from the group consisting of hydrogen, an alkali metal counterion, and a counterion derived from an organic base wherein the organic base is selected from the group consisting trimethylamine, diethylamine, ethanolamine, piperidine, isopropylamine, choline, and caffeine; and $R^3$ is $-(CH_2)_2-$.

2. A compound as in claim 1, wherein R is isopropyl.

3. A compound as in claim 1, wherein X and Y are lithium.

4. A compound having the formula:

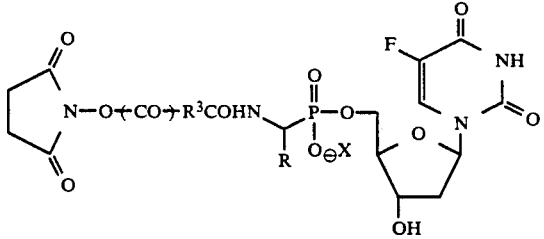

in which R is selected from the group consisting of hydrogen, methyl, isopropyl, isobutyl, sec-butyl, and 4-hydroxybenzyl; X and Y are independently selected form the group consisting of hydrogen, an alkali metal counterion, and a counterion derived from an organic base wherein the organic base is selected from the group consisting of trimethylamine, diethylamine, ethanolamine, piperidine, isopropylamine, choline, and caffeine; and $R^3$ is $-(CH_2)_2-$.

5. A compound as in claim 4, wherein R is isopropyl.

6. A compound as in claim 4, wherein X is lithium.

7. A compound having the formula:

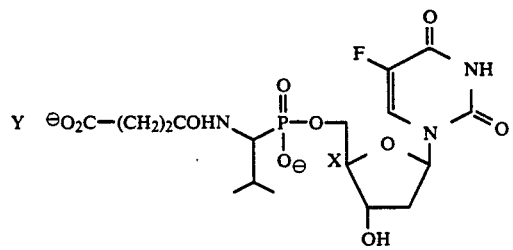

which X and Y are independently selected from the group consisting of hydrogen, an alkali metal counterion, and a counterion derived from an organic base wherein the organic base is selected from the group consisting of trimethylamine, diethylamine, ethanolamine, piperidine, isopropylamine, choline, and caffeine.

8. A compound having the formula:

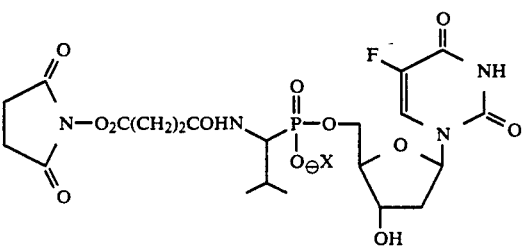

in which X is selected from the group consisting of hydrogen, an alkali metal counterion, and a counterion derived from an organic base wherein the organic base is selected from the group consisting of trimethylamine, diethylamine, ethanolamine, piperidine, isopropylamine, choline, and caffeine.

* * * * *